(12) United States Patent
Ohgishi et al.

(10) Patent No.: US 8,696,583 B2
(45) Date of Patent: Apr. 15, 2014

(54) ULTRASOUND ENDOSCOPE

(71) Applicant: Olympus Medical Systems Corp., Tokyo (JP)

(72) Inventors: Kozue Ohgishi, Sagamihara (JP); Kei Irie, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/764,881

(22) Filed: Feb. 12, 2013

(65) Prior Publication Data

US 2013/0158410 A1    Jun. 20, 2013

Related U.S. Application Data

(63) Continuation of application No. PCT/JP2012/060558, filed on Apr. 19, 2012.

(30) Foreign Application Priority Data

Sep. 9, 2011    (JP) .................................. 2011-197506

(51) Int. Cl.
*A61B 8/14*        (2006.01)
(52) U.S. Cl.
USPC .......................................... 600/459; 600/462
(58) Field of Classification Search
USPC ................................................. 600/459, 462
See application file for complete search history.

(56) References Cited

U.S. PATENT DOCUMENTS

| | | | | |
|---|---|---|---|---|
| 5,176,140 A | * | 1/1993 | Kami et al. ................... | 600/459 |
| 5,320,104 A | * | 6/1994 | Fearnside et al. ............. | 600/463 |
| 5,351,691 A | * | 10/1994 | Brommersma ............... | 600/462 |
| 5,353,798 A | * | 10/1994 | Sieben .......................... | 600/462 |
| 5,479,930 A | * | 1/1996 | Gruner et al. ................. | 600/459 |
| 5,634,466 A | * | 6/1997 | Gruner .......................... | 600/459 |
| 5,669,389 A | * | 9/1997 | Rotteveel et al. ............. | 600/459 |
| 5,884,627 A | * | 3/1999 | Wakabayashi et al. ....... | 600/447 |

(Continued)

FOREIGN PATENT DOCUMENTS

| | | |
|---|---|---|
| JP | 2002-306490 | 10/2002 |
| JP | 2004-209044 | 7/2004 |

(Continued)

OTHER PUBLICATIONS

European Search Report dated Oct. 15, 2013 issued in European Patent Application No. 12829864.3.

*Primary Examiner* — Long V. Le
*Assistant Examiner* — Nicholas Evoy
(74) *Attorney, Agent, or Firm* — Scully, Scott, Murphy & Presser, P.C.

(57) ABSTRACT

An ultrasound endoscope has a transducer unit that has a top surface, a bottom surface and a side surface connecting the top surface and the bottom surface, and performs transmission and reception of ultrasound on a top surface side, a cable that is for transmitting and receiving an electrical signal to and from the transducer unit and is connected to the side surface, a conductive shield case that has a lead-out port for leading out the cable, and a flexible extension portion extended from at least the top surface side of the lead-out port, and covers the side surface and the bottom surface, and a housing that holds a transducer unit 2 via the shield case, and has a cable insertion path in which the cable and the extension portion are inserted.

9 Claims, 17 Drawing Sheets

(56) References Cited

U.S. PATENT DOCUMENTS

| | | | |
|---|---|---|---|
| 6,017,311 A * | 1/2000 | Sakamoto | 600/459 |
| 6,039,695 A * | 3/2000 | Sakamoto et al. | 600/459 |
| 6,425,870 B1 * | 7/2002 | Flesch | 600/459 |
| 6,719,694 B2 * | 4/2004 | Weng et al. | 600/439 |
| 7,520,856 B2 * | 4/2009 | Vaezy et al. | 600/439 |
| 7,625,342 B2 * | 12/2009 | Morokawa et al. | 600/459 |
| 7,798,971 B2 * | 9/2010 | Flesch et al. | 600/459 |
| 2004/0073118 A1 * | 4/2004 | Peszynski et al. | 600/459 |
| 2005/0096542 A1 * | 5/2005 | Weng et al. | 600/439 |
| 2005/0228289 A1 | 10/2005 | Kohno | |
| 2006/0241472 A1 * | 10/2006 | Osawa et al. | 600/459 |
| 2008/0300492 A1 * | 12/2008 | Nagano et al. | 600/462 |
| 2008/0306389 A1 * | 12/2008 | Nagano et al. | 600/462 |
| 2009/0088646 A1 * | 4/2009 | Nagano et al. | 600/463 |
| 2009/0088647 A1 * | 4/2009 | Nagano et al. | 600/463 |
| 2009/0234233 A1 * | 9/2009 | Nagano et al. | 600/462 |
| 2009/0281429 A1 * | 11/2009 | Nishina et al. | 600/459 |
| 2010/0256499 A1 * | 10/2010 | Imahashi | 600/459 |
| 2011/0060328 A1 * | 3/2011 | Skwarek et al. | 606/33 |
| 2011/0112405 A1 * | 5/2011 | Barthe et al. | 600/459 |

FOREIGN PATENT DOCUMENTS

| | | |
|---|---|---|
| JP | 2009-082360 | 4/2009 |
| JP | 2009-240755 | 10/2009 |
| WO | WO 94/16625 A1 | 8/1994 |

* cited by examiner

ULTRASOUND ENDOSCOPE

CROSS REFERENCE TO RELATED APPLICATION

This application is a continuation application of PCT/JP2012/060558 filed on Apr. 19, 2012 which claims benefit of Japanese Application No. 2011-197506 filed in Japan on Sep. 9, 2011, the entire contents of which are incorporated herein by this reference.

BACKGROUND OF THE INVENTION

1. Field of the Invention

The present invention relates to an ultrasound endoscope.

2. Description of the Related Art

Conventionally, in a medical field, ultrasound endoscope apparatuses have been widely used. In an ultrasound endoscope, an ultrasound probe which performs transmission and reception of ultrasound is provided at a distal end portion of an elongated endoscope insertion portion. An ultrasound endoscope apparatus transmits ultrasound from an ultrasound probe thereof, and generates an ultrasound image of a subject from an ultrasound echo signal received from the subject and displays the ultrasound image.

A transducer unit having a transducing portion is disposed in an interior of the ultrasound probe provided at a distal end portion of an insertion portion of an ultrasound endoscope. The transducer unit is housed in a housing. Further, the transducer unit is provided in a shield case which is grounded in consideration of electrical safety, countermeasures against noise and the like for a subject, because the insertion portion is inserted into the subject.

When a distal end portion unit including the transducer unit is assembled, the transducer unit to which an elongated cable unit is connected is housed in a shield case first. Subsequently, the transducer unit to which the elongated cable unit is connected is housed into the housing in such a manner as to be forced into the housing, whereby the distal end portion unit of the ultrasound endoscope is assembled. As a result, the transducer unit housed in the shield case is housed in the housing at the distal end portion of the insertion portion.

Further, as a countermeasure against heat that is generated by ultrasound vibration in an ultrasound endoscope, for example, Japanese Patent Application Laid-Open Publication No. 2009-240755 proposes and discloses the art of providing a highly thermal conductive layer at a distal end portion.

SUMMARY OF THE INVENTION

An ultrasound endoscope of one aspect of the present invention has an ultrasound transmitting and receiving portion that has a top surface, a bottom surface and a side surface that connects the top surface and the bottom surface, and performs transmission and reception of ultrasound on the top surface side, a cable that is for transmitting and receiving an electrical signal to and from the ultrasound transmitting and receiving portion and is connected to the side surface, a conductive shield case that has a lead-out port for leading out the cable, and a flexible extension portion extended from at least the top surface side of the lead-out port, and covers the side surface and the bottom surface, and a housing that holds the ultrasound transmitting and receiving portion via the shield case, and has a cable insertion path in which the cable and the extension portion are inserted.

DETAILED DESCRIPTION OF THE PREFERRED EMBODIMENTS

Figure 1:
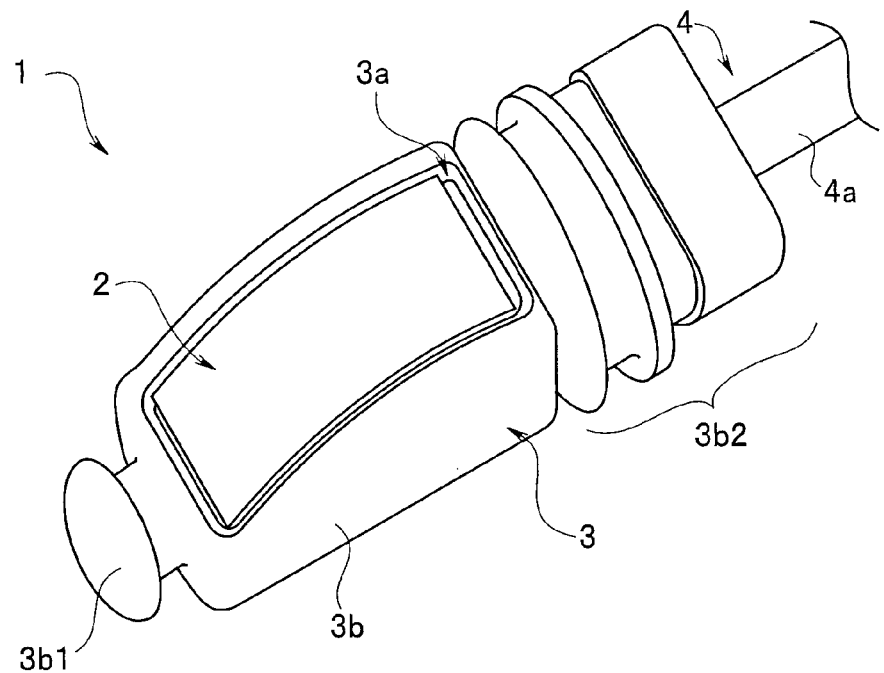
FIG. 1 is a perspective view of a distal end portion unit according to a first embodiment of the present invention seen from diagonally above a front side of the distal end portion unit.

Hereinafter, embodiments of the present invention will be described with reference to the drawings.

In the respective drawings used in the following description, a scale is made to differ at each of the respective components in order to make the respective components have such sizes as to be recognizable on the drawings, and the present invention is not limited to only the numbers and the amounts of the components, the shapes of the components, the ratios of the sizes of the components, and the relative positional relations of the respective components which are illustrated in the drawings.

(First Embodiment)

Figure 2:
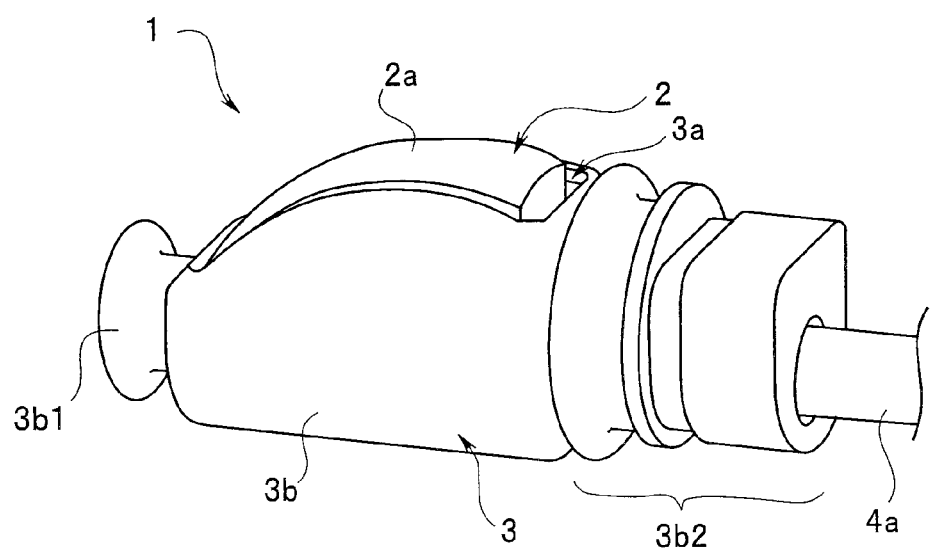
FIG. 2 is a perspective view of the distal end portion unit according to the first embodiment of the present invention seen from a slightly diagonally rear of a side of the distal end portion unit.
Figure 3:
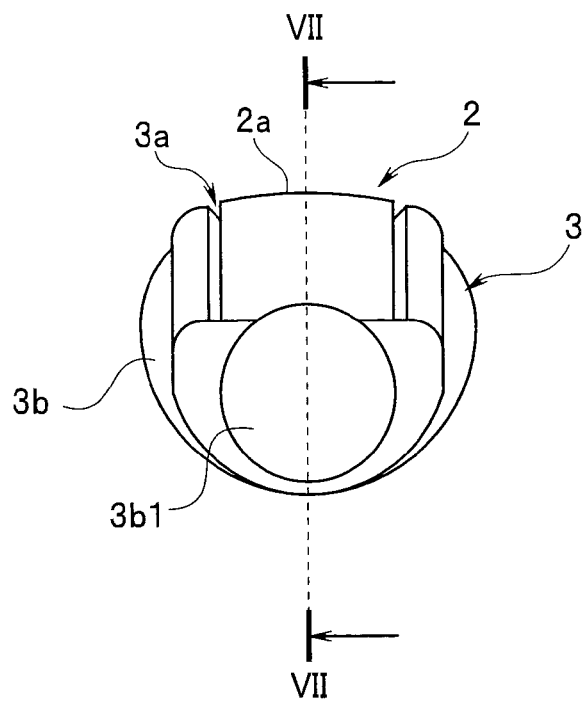
FIG. 3 is a view of a distal end portion unit 1 according to the first embodiment of the present invention seen from a front side in an axial direction of the distal end portion unit 1.

FIGS. 1 and 2 are external appearance views of a distal end portion unit of an ultrasound endoscope according to a first embodiment of the present invention. FIG. 1 is a perspective view of the distal end portion unit seen from diagonally above a front side of the distal end portion unit. FIG. 2 is a perspective view of the distal end portion unit seen from a slightly diagonally rear of a side of the distal end portion unit. FIG. 3 is a view of a distal end portion unit 1 seen from a front side in an axial direction of the distal end portion unit 1.

The distal end portion unit 1 is configured by mainly having a transducer unit 2, a housing 3, a cable unit 4 and a shield case 5 (not illustrated in FIG. 1, FIG. 2 and FIG. 3). The distal end portion unit 1 is configured in such a manner that the transducer unit 2 is housed in a housing portion 3a of the housing 3, and a cable 4a of the cable unit 4 is extended from a proximal end side of the housing 3. An endoscope distal end portion is configured by the distal end portion unit 1 being provided in a distal end rigid member of an insertion portion of the ultrasound endoscope.

The transducer unit 2 which is an ultrasound transmitting and receiving portion has an ultrasound transducer in an interior thereof. An acoustic lens surface 2a which focuses ultrasound is provided on a top surface side of the transducer unit 2. A lower portion of the transducer unit 2 is housed in the shield case 5 which will be described later.

The transducer unit 2 has a top surface, a bottom surface and side surfaces which connect the top surface and the bottom surface, and configures the ultrasound transmitting and receiving portion which performs transmission and reception of ultrasound on the top surface side. In this case, the acoustic lens surface 2a is located on the top surface.

The housing 3 is made of a resin, and has a housing main body portion 3b, a protruding portion 3b1 having a flange portion formed at a distal end portion of the housing main body portion 3b, and a proximal end portion 3b2. A cable 4a is extended from the proximal end portion 3b2. The cable 4a is connected to the side surface of the transducer unit 2 to transmit and receive electrical signals to and from the transducer unit 2 which is the ultrasound transmitting and receiving portion.

An opening portion of the housing portion 3a of the housing main body portion 3b has a shape along a shape of the acoustic lens surface 2a of the transducer unit 2. An internal structure of the housing 3 will be described later.

Note that in the present embodiment and the following descriptions (descriptions of modifications and another embodiment), the ultrasound transmitting and receiving portions are described as convex type ultrasound transmitting and receiving portions, but may be concave type ultrasound transmitting and receiving portions.

Figure 4:
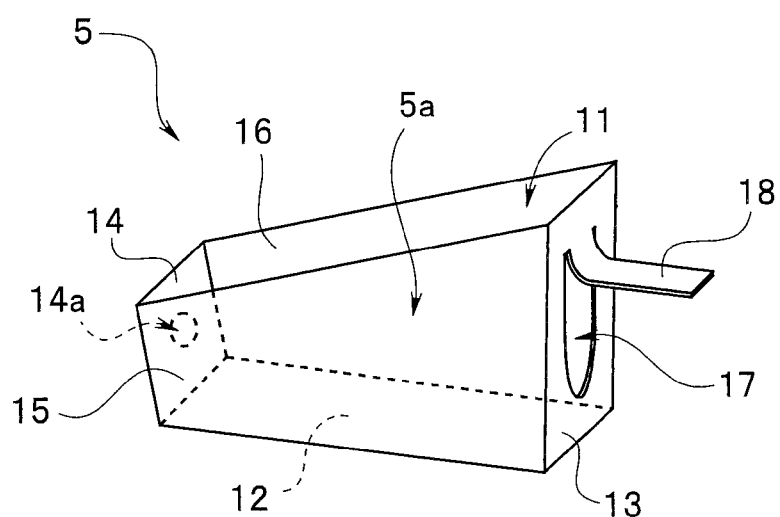
FIG. 4 is a perspective view of a shield case 5 according to the first embodiment of the present invention.
Figure 5:
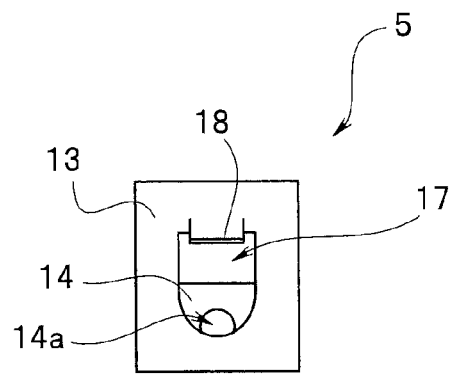
FIG. 5 is a view of the shield case 5 according to the first embodiment of the present invention seen from a proximal end direction.

FIG. 4 is a perspective view of the shield case 5. FIG. 5 is a view of the shield case 5 seen from a proximal end direction. The shield case 5 has an opening portion 11, a bottom surface portion 12 and four side surface portions 13, 14, 15 and 16. The shield case 5 is made of a metal, and has a box shape which is opened to an upper side with an area of the opening portion 11 on the top surface being larger than an area of the bottom surface portion 12. Therefore, a housing portion 5a is formed by the bottom surface portion 12 and the four side surface portions 13, 14, 15 and 16.

More specifically, the shield case 5 is configured such that the side surface portions 13, 15 and 16 at a proximal end side are orthogonal to the bottom surface portion 12, and the side surface portion 14 at a distal end side forms an angle of 90 degrees or more with the bottom surface portion 12.

Further, a height of the side surface portion 13 at the proximal end side, from the bottom surface portion 12 is higher than a height of the side surface portion 14 at the distal end side, from the bottom surface portion 12, and therefore, the opening portion 11 is formed in a slanting state with respect to the bottom surface portion 12.

A lead-out port 17 for leading the cable 4a of the cable unit 4 to an outside of the shield case 5 is formed at the side surface portion 13 at the proximal end side. As shown in FIG. 5, the lead-out port 17 is semi-circular at a bottom surface side, is rectangular at a top surface side, and has such a size that the cable 4a can be inserted therethrough.

Furthermore, a plate-shaped extension portion 18 which extends in a proximal end direction is formed at an upper side of the side surface portion 16, that is, a top surface side of the lead-out port 17. The extension portion 18 is formed at a position where an upper side surface of the cable 4a which extends from the transducer unit 2 abuts on an undersurface of the extension portion 18 when the transducer unit 2 is housed in the shield case 5.

Namely, the shield case 5 is a conductive member that has the lead-out port 17 for leading out the cable 4a, and the flexible extension portion 18 that is extended from at least the top surface side of the lead-out port 17, and covers the side surfaces and the bottom surface of the transducer unit 2.

The shield case 5 is produced by one metal sheet material being subjected to work such as folding or brazing. In the present embodiment, the extension portion 18 is made of a metal and has flexibility, and the shield case 5 and the extension portion 18 are produced by folding work.

For example, a length of the extension portion 18 is 1 to 3 mm and a thickness thereof is 0.2 mm. Note that for the extension portion 18, a material having elasticity is preferable, as will be described later. As a metal having elasticity, for example, copper and phosphor bronze are cited.

As shown in FIG. 4 and FIG. 5, a through hole 14a is provided at the side surface portion 14 of the distal end side of the shield case 5, and the shield case 5 is configured so that grounding wiring in an interior is led out to an outside of the shield case 5 via the through hole 14a and the grounding wiring can be soldered at the outside of the shield case 5.

Figure 6:
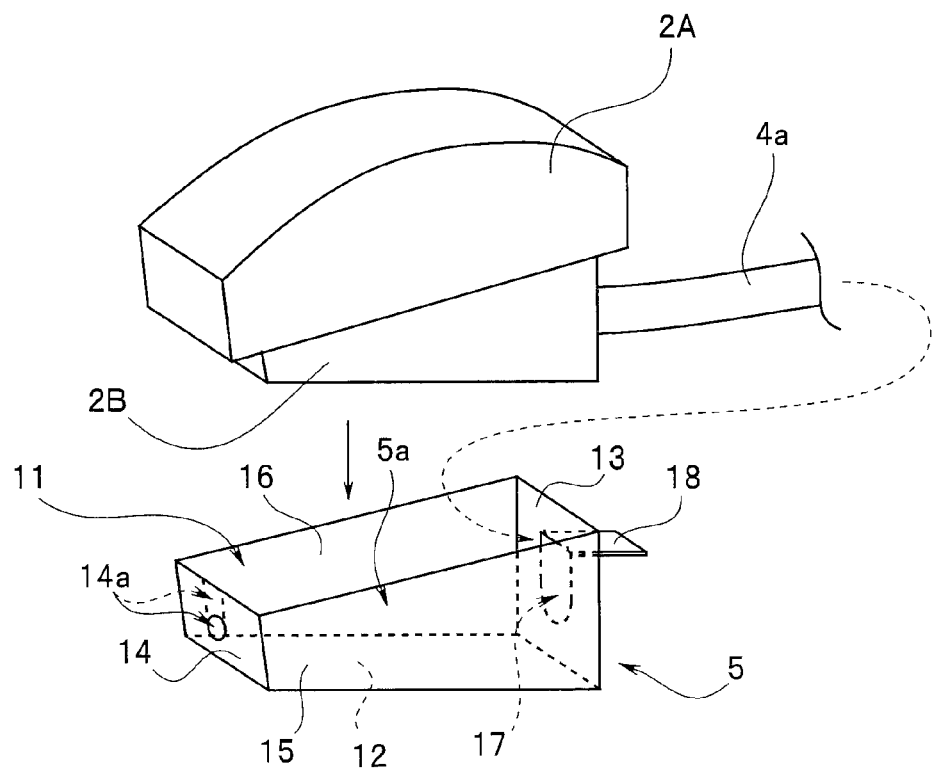
FIG. 6 is a view for explaining housing of a transducer unit 2 into the shield case 5, according to the first embodiment of the present invention.

Note that in order to lead the grounding wiring to the outside of the shield case 5, a U-shaped cutout may be formed at the side surface portion 14 at the distal end side as shown by the dotted line in FIG. 6, in place of the circular through hole 14a.

The through hole 14a as above is provided, whereby wiring by soldering or the like can be made at the outside of the shield case 5, and therefore, favorable operability is provided. Further, a wiring spot is located at the distal end side of the shield case 5, and therefore, the distal end portion of the ultrasound endoscope is made compact.

Furthermore, a conductor plate (not illustrated) in the transducer unit 2 and the side surface portion of the shield case 5 are disposed on the same plane, whereby both of the conductor plate and the shield case 5 can be disposed without a gap, and the wiring portion can be completely covered with a metal member. Therefore, reliable grounding can be performed.

Furthermore, the wiring portion protrudes to the distal end side from the acoustic lens surface 2a of the transducer unit 2, and therefore, even when an insulative member in the transducer unit 2 is broken, an electric current does not flow to a so-called patient circuit.

FIG. 6 is a view for explaining housing of the transducer unit 2 into the shield case 5. The transducer unit 2 of the present embodiment includes an upper portion 2A including an ultrasound transducer, the acoustic lens and the like, and a lower portion 2B including a circuit board and the like. The upper portion 2A is larger than the lower portion 2B, and the lower portion 2B has a shape corresponding to a shape of the housing portion 5a of the shield case 5.

When the transducer unit 2 is housed into the shield case 5, a proximal end portion of the cable 4a of the cable unit 4 is inserted through the lead-out port 17 from an inside of the shield case 5 first, and the cable 4a is passed into the lead-out port 17 up to a distal end portion of the cable 4a. Subsequently, the lower portion 2B of the transducer unit 2 is housed into the shield case 5 in such a manner that the distal end portion of the cable 4a is pressed against an inside of the lead-out port 17. In this manner, the lower portion 2B of the transducer unit 2 is housed into the housing portion 5a of the shield case 5.

Figure 7:
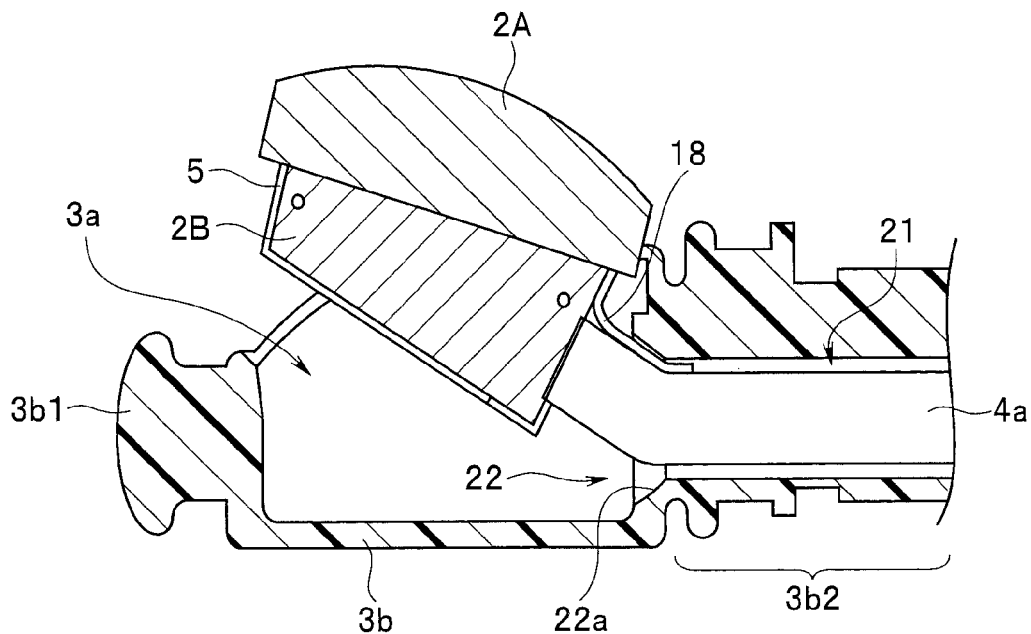
FIG. 7 is a sectional view for explaining a process of the transducer unit 2 to which a cable unit 4 is connected being fitted into a housing portion 3a of a housing 3, according to the first embodiment of the present invention.

FIG. 7 is a sectional view for explaining a process of the transducer unit 2 to which the cable unit 4 is connected being fitted into the housing portion 3a of the housing 3.

First, with reference to FIG. 7, a structure of an interior of the housing 3 will be described. The housing portion 3a is formed in the housing main body portion 3b of the housing 3 having a substantially circular column-shape. The housing portion 3a is a recessed portion formed in the housing main body portion 3b, and has such a size that the transducer unit 2 can be housed therein. A cable insertion path 21 that communicates with the housing portion 3a is provided at the proximal end portion 3b2. An opening portion 22 of the cable insertion path 21 is formed at a proximal end side of the housing portion 3a. A taper portion 22a for enhancing insertability of the cable 4a is formed at the opening portion 22.

Therefore, the housing 3 holds the transducer unit 2 via the shield case 5, and has the cable insertion path 21 in which the cable 4a and the extension portion 18 are inserted.

When the transducer unit 2 is fitted into the housing portion 3a of the housing 3, the proximal end portion of the cable 4a is firstly passed through the cable insertion path 21 from the opening portion 22, the cable 4a is led out, and the distal end portion of the cable 4a, that is, a connection portion of the cable unit 4 and the transducer unit 2 is caused to be close to the opening portion 22. Subsequently, a distal end portion of the extension portion 18 of the shield case 5 is inserted into the cable insertion path 21 from the opening portion 22 of the housing portion 3a, as shown in FIG. 7.

At this time, as shown in FIG. 7, a proximal end portion of the extension portion 18 is inserted into the cable insertion path 21 from the opening portion 22 of the housing portion 3a while the extension portion 18 abuts and slides on the upper side of an end portion of the opening portion 22. Further, when the extension portion 18 has elasticity, an operator can insert the extension portion 18 into the cable insertion path 21 in such a manner that the extension portion 18 is naturally drawn into the cable insertion path 21 by springiness of the extension portion 18. Further, the taper portion 22a is formed at the opening portion 22, and therefore, the transducer unit 2 can be housed more easily.

Furthermore, in the process of housing the transducer unit 2 into the housing portion 3a of the housing 3, the connection portion of the cable unit 4 and the transducer unit 2 is protected by the extension portion 18, and bending stress to the connection portion of the cable unit 4 and the transducer unit 2, which is applied at the time of housing of the transducer unit 2 into the housing portion 3a of the housing 3 is relieved.

Figure 8:
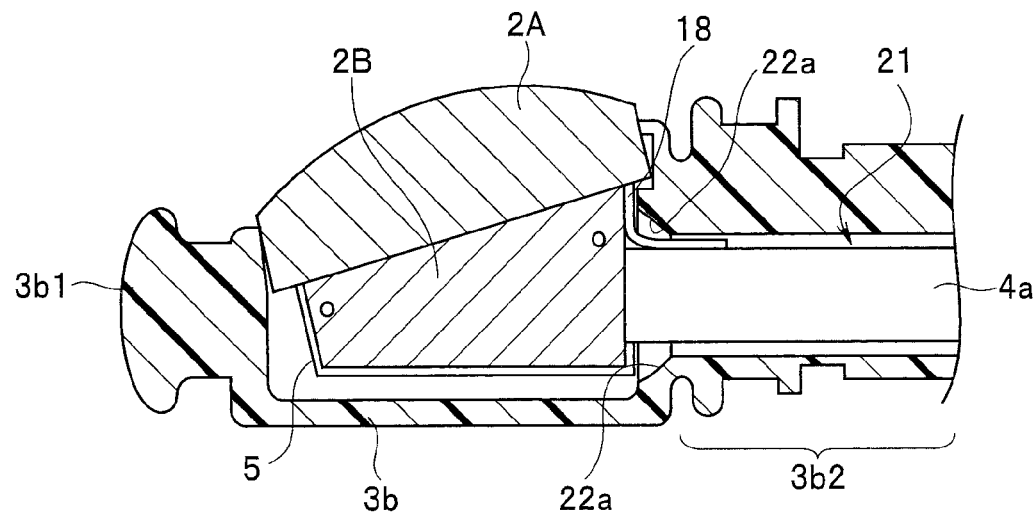
FIG. 8 is a sectional view showing a state in which the transducer unit 2 is housed in the housing portion 3a of the housing 3, according to the first embodiment of the present invention.

Namely, as shown in FIG. 7, the transducer unit 2 is fitted in from an oblique direction with respect to an axis of the cable insertion path 21 of the proximal end portion 3b2, but the bending stress which is concentrated on the connection portion of the transducer unit 2 and the cable unit 4 is relieved by the extension portion 18, and therefore, a damage to a signal line in the cable unit 4 is hardly caused. As a result, breakage of the internal signal line hardly occurs. FIG. 8 is a sectional view showing a state in which the transducer unit 2 is housed in the housing portion 3a of the housing 3.

Consequently, according to the configuration described above, at the time of assembly of the ultrasound endoscope, stress concentration to the connection portion of the transducer unit and the cable unit is relieved, buckling of the cable end is prevented, and damage, breakage and the like of the signal line of the cable can be prevented. Furthermore, according to the present embodiment described above, assemblability of the distal end portion unit is enhanced, and yield is enhanced, which also leads to reduction of cost by extension.

Note that a groove in which the plate-shaped extension portion 18 is fitted is provided along the inside of the cable insertion path 21 from the opening portion 22 of the housing portion 3a, a width of the groove (width in the direction orthogonal to an axial direction of the cable insertion path 21) is made substantially the same as a width of the extension portion 18, and the extension portion 18 is inserted into the groove, whereby positioning around an axis of the transducer unit 2 can be reliably performed. Namely, the width of the groove provided at the top surface side of the opening portion 22 is made to have such a size that the extension portion 18 can be fitted therein, but does not rotate around the axis, whereby positioning around the axis of the transducer unit 2 which is housed in the housing portion 3*a* can be performed.

Note that the extension portion 18 can adopt the configurations of various modifications, and may have the following configurations.

(Modification 1)

Figure 9:
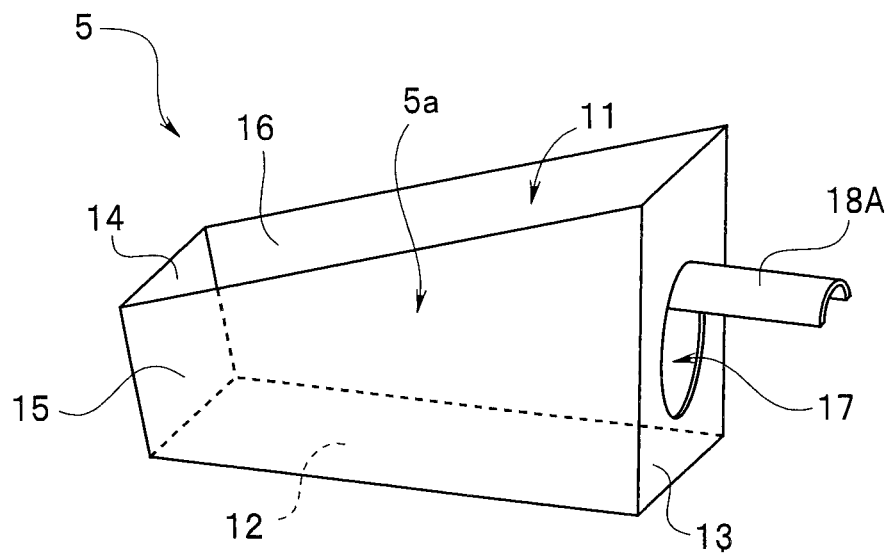
FIG. 9 is a perspective view of the shield case 5 having an extension portion according to modification 1 of the first embodiment of the present invention.
Figure 10:
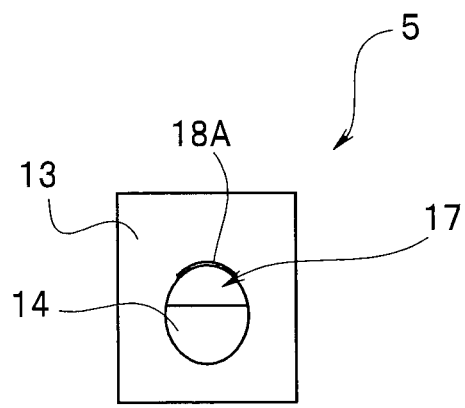
FIG. 10 is a view of the shield case 5 having the extension portion according to modification 1 of the first embodiment of the present invention seen from a proximal end direction.

FIG. 9 and FIG. 10 are views for explaining the extension portion according to the present modification 1. FIG. 9 is a perspective view of the shield case 5 having the extension portion according to modification 1. FIG. 10 is a view of the shield case 5 seen from a proximal end direction. In FIG. 9 and FIG. 10, the same components as in the embodiment described above are assigned with the same reference signs, and the description thereof will be omitted.

As shown in FIG. 9, an extension portion 18A of the present modification is disposed at the top surface side of the lead-out port 17, and has a shape of a curved surface projected to the top surface side. More specifically, the extension portion 18A has a tub shape along a part of the shape of the lead-out port 17, as shown in FIG. 10.

The extension portion 18A of the present modification has the shape of the curved surface projected to the upper side, and therefore, when bending stress is applied to the connection portion of the transducer unit 2 and the cable unit 4, a force which is generated as reaction is larger in the extension portion 18A than in the extension portion 18 as shown in FIG. 4.

Consequently, the extension portion 18A of the present modification generates the similar effect to the extension portion 18 of the embodiment described above, and also provides the effect of being capable of making the thickness of the extension portion 18A small.

(Modification 2)

Figure 11:
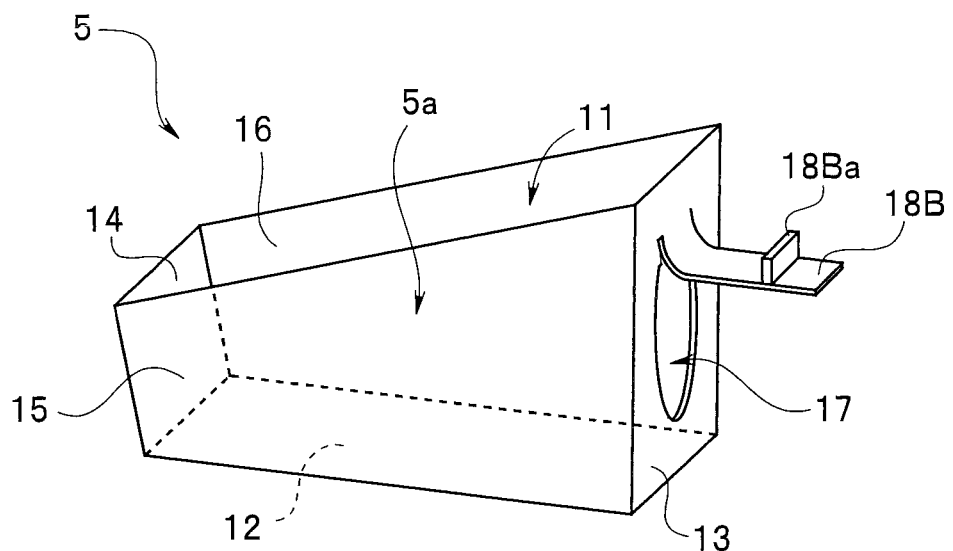
FIG. 11 is a perspective view of the shield case 5 having an extension portion according to modification 2 of the first embodiment of the present invention.
Figure 12:
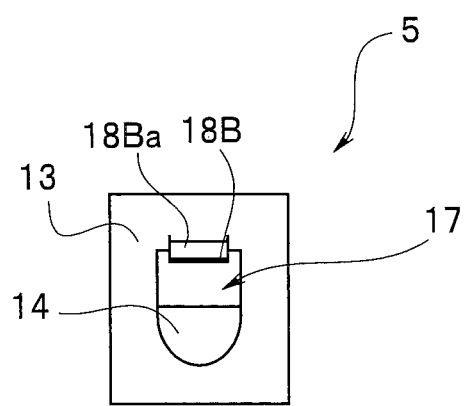
FIG. 12 is a view of the shield case 5 having the extension portion according to modification 2 of the first embodiment of the present invention seen from the proximal end direction.
Figure 13:
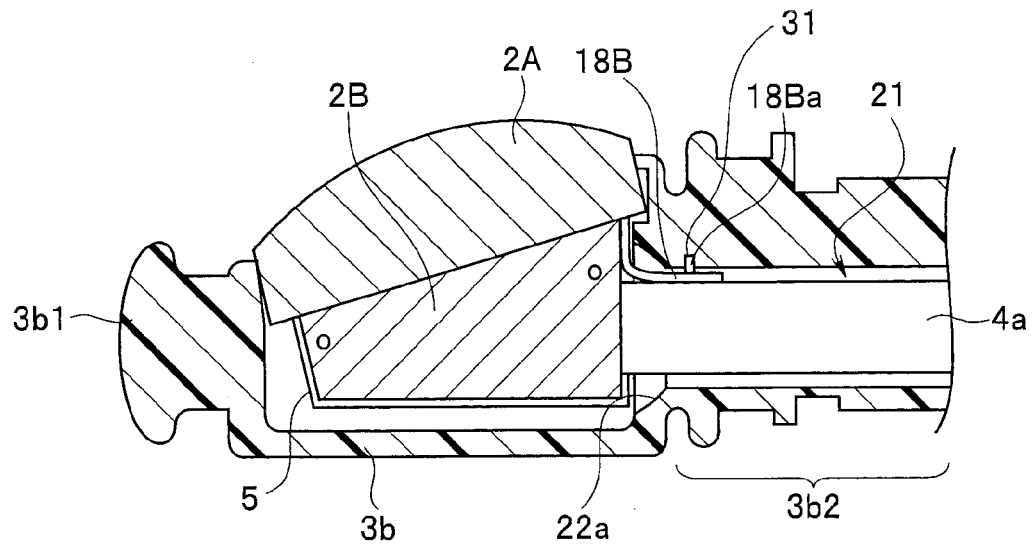
FIG. 13 is a sectional view showing a state in which the transducer unit 2 is housed in the housing portion 3a of the housing 3, according to modification 2 of the first embodiment of the present invention.

FIG. 11, FIG. 12 and FIG. 13 are views for explaining an extension portion according to the present modification 2. FIG. 11 is a perspective view of the shield case 5 having the extension portion according to the present modification 2. FIG. 12 is a view of the shield case 5 having the extension portion according to the present modification 2 seen from a proximal end direction. FIG. 13 is a sectional view showing a state in which the transducer unit 2 is housed in the housing portion 3*a* of the housing 3. In FIG. 11 to FIG. 13, the same components as in the embodiment described above are assigned with the same reference signs, and the description thereof will be omitted.

As shown in FIG. 11, an extension portion 18B of the present modification is plate-shaped, and has a projected portion 18Ba which is projected to the top surface side at a part of the extension portion 18B. A recessed portion 31 which is formed to be recessed is provided at a part of an inner surface of the cable insertion path 21. As shown in FIG. 13, the projected portion 18Ba is provided to be in such a shape and position as to be fitted in the recessed portion 31 formed at the inner surface of the cable insertion path 21 when the transducer unit 2 is housed into the housing portion 3*a* of the housing 3.

Consequently, a projected amount of the projected portion 18Ba to the upper side has to be such an amount that the extension portion 18B and the cable 4*a* to be inserted into the cable insertion path 21.

The extension portion 18B of the present modification has the projected portion 18Ba, the inner surface of the cable insertion path 21 has the recessed portion 31, the projected portion 18Ba and the recessed portion 31 are fitted to each other, and positioning of the transducer unit 2 is reliably performed. Namely, when the transducer unit 2 is housed in the housing 3 via the shield case 5, the recessed portion 31 and the projected portion 18Ba are fitted to each other.

Consequently, the extension portion 18B of the present modification generates the similar effect to the extension portion 18 of the embodiment described above, and also provides the effect of being capable of reliably performing positioning in an axial direction of the transducer unit 2, and being capable of reducing variation in assembly among products by extension.

In the present modification, the projected portion 18Ba is provided at the extension portion 18B, whereas the recessed portion 31 is provided at the inner surface of the cable insertion path 21. However, the recessed portion may be provided at the extension portion 18B, and the projected portion may be provided at the inner surface of the cable insertion path 21.

(Modification 3)

Figure 14:
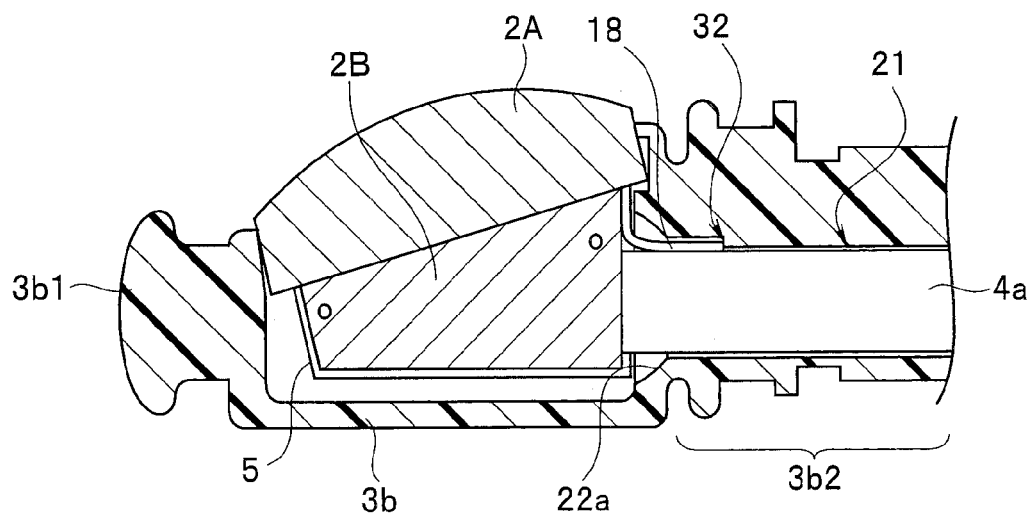
FIG. 14 is a sectional view showing a state in which the transducer unit 2 is housed in the housing portion 3a of the housing 3, according to modification 3 of the first embodiment of the present invention.

FIG. 14 is a view for explaining an extension portion according to the present modification 3. FIG. 14 is a sectional view showing a state in which the transducer unit 2 is housed in the housing portion 3*a* of the housing 3, according to the present modification 3. In FIG. 14, the same components as in the embodiment described above are assigned with the same reference signs, and the description thereof will be omitted.

As shown in FIG. 14, in the present modification, a step portion 32 on which the distal end portion of the extension portion 18 or 18A abuts when the transducer unit 2 is housed into the housing portion 3*a* of the housing 3 is formed at the upper side of the inner surface of the cable insertion path 21.

In the present modification, the distal end portion of the extension portion 18 or 18A abuts on the step portion 32 formed on the inner surface of the cable insertion path 21, and positioning of the transducer unit 2 is reliably performed.

Consequently, in the configuration of the present modification, the similar effect to the extension portion 18 of the embodiment described above is also generated, and the effect of being capable of reliably performing positioning in the axial direction of the transducer unit 2 is also provided.

(Modification 4)

Figure 15:
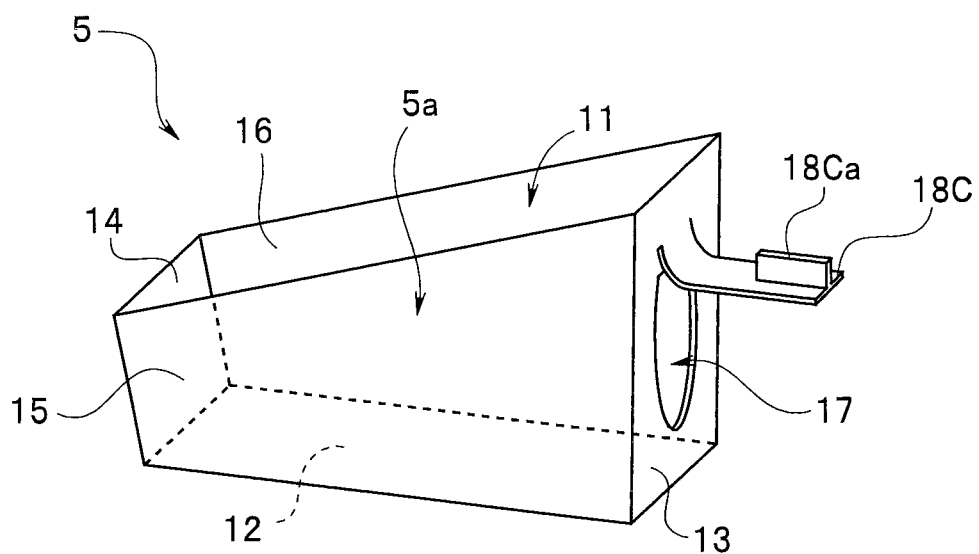
FIG. 15 is a perspective view of the shield case 5 having an extension portion according to modification 4 of the first embodiment of the present invention.
Figure 16:
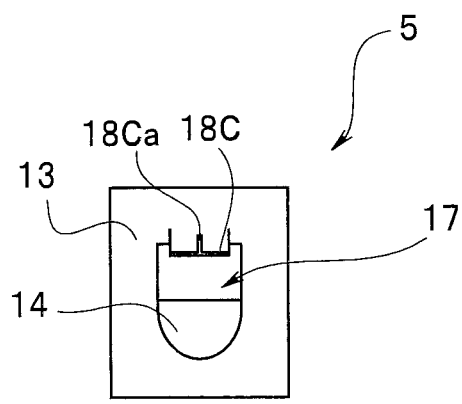
FIG. 16 is a view of the shield case 5 having the extension portion according to modification 4 of the first embodiment of the present invention seen from the proximal end direction.
Figure 17:
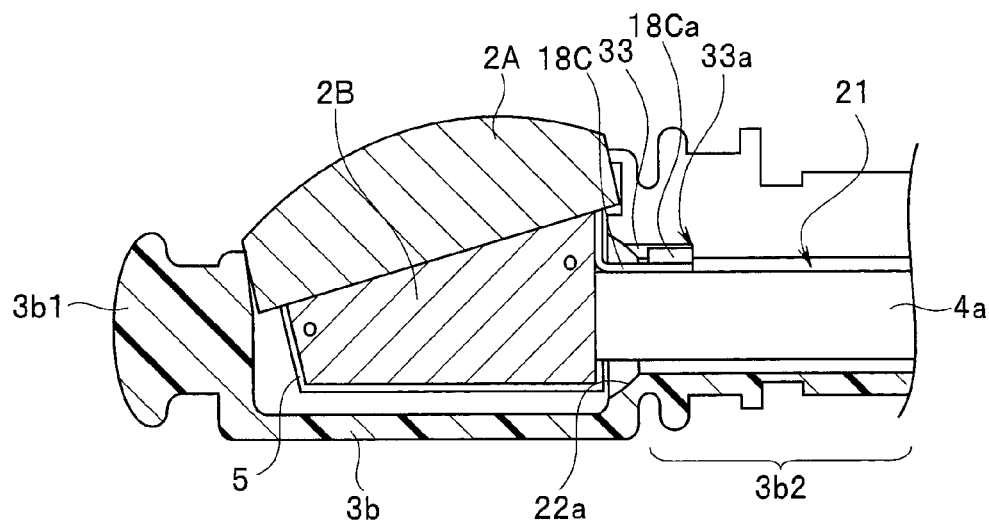
FIG. 17 is a sectional view showing a state in which the transducer unit 2 is housed in the housing portion 3a of the housing 3 according to modification 4 of the first embodiment of the present invention.

FIG. 15, FIG. 16 and FIG. 17 are views for explaining an extension portion according to the present modification 4. FIG. 15 is a perspective view of the shield case 5 having the extension portion according to the present modification 4. FIG. 16 is a view of the shield case 5 having the extension portion according to the present modification 4 seen from a proximal end direction. FIG. 17 is a sectional view showing a state in which the transducer unit 2 is housed in the housing portion 3*a* of the housing 3. In FIG. 15 to FIG. 17, the same components as in the embodiment described above are assigned with the same reference signs, and the description thereof will be omitted.

As shown in FIG. 15, an extension portion 18C of the present modification is plate-shaped, and has a protruded portion 18Ca which is formed at the top surface side along an extending direction of the extension portion 18C. A groove 33 which is a depressed portion in which the protruded portion 18Ca is engaged or fitted is formed on the inner surface of the housing portion 3*a* of the housing 3. A width of the groove portion 33 in a circumferential direction of the housing portion 3*a* of the housing 3 has such a size that the protruded portion 18Ca is fitted in the groove portion 33.

Namely, as shown in FIG. 17, the protruded portion 18Ca has such a shape as to be engaged in the groove portion 33 which is formed along the axial direction on the inner surface of the cable insertion path 21 when the transducer unit 2 is housed into the housing portion 3*a* of the housing 3.

Consequently, the extension portion 18C of the present modification generates the similar effect to the extension portion 18 of the embodiment described above, and has the effect of being capable of reliably performing positioning around the axis of the transducer unit 2.

In the present modification, a distal end portion of the extension portion 18C (proximal end portion of the protruded portion 18Ca in FIG. 17) abuts on a step portion 33a at the proximal end side of the groove portion 33 which is formed on the inner surface of the cable insertion path 21, and therefore, positioning in the axial direction of the transducer unit 2 is also reliably performed.

Furthermore, the protruded portion 18Ca can be also provided at the upper sides of the extension portions 18A and 18B of modifications 1 and 2.

As above, according to the present embodiment and the respective modifications described above, the ultrasound endoscope can be provided, which is capable of preventing damage, breakage and the like of the signal line of the cable by relieving stress concentration to the connection portion of the transducer unit and the cable unit at the time of assembly of the ultrasound endoscope.

(Second Embodiment)

In the first embodiment, the extension portion 18 or the like is in the flat plate shape or the plate shape having the curved surface formed at the upper side of the lead-out port 17 of the shield case 5, and an extension portion of the present embodiment differs from the first embodiment in the point that the extension portion is a coil spring member. In the present embodiment, the same components as in the first embodiment are assigned with the same reference signs, and the description thereof will be omitted.

Figure 18:
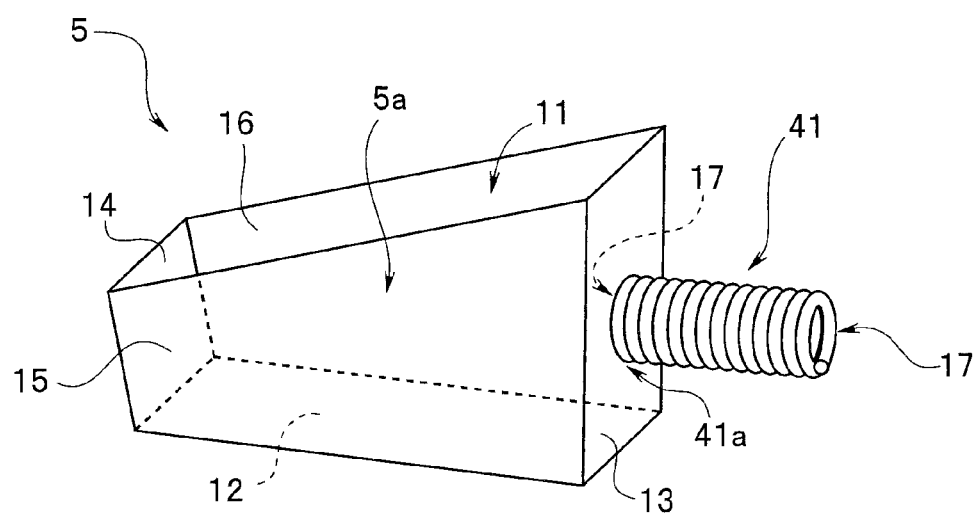
FIG. 18 is a perspective view of the shield case 5 having the extension portion according to a second embodiment of the present invention.
Figure 19:
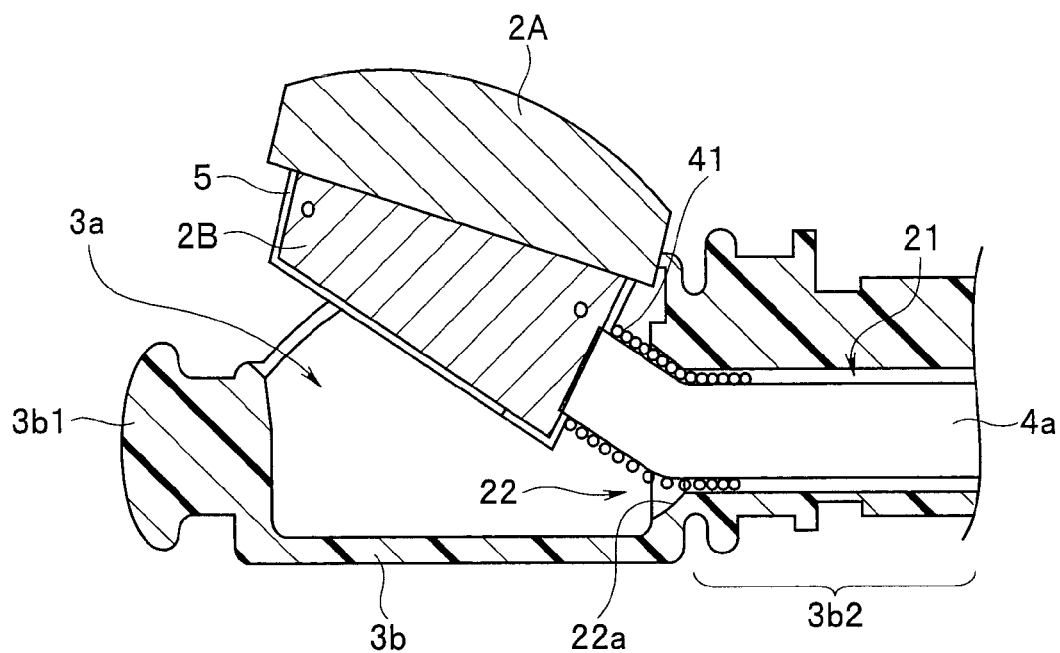
FIG. 19 is a sectional view for explaining a process of the transducer unit 2 to which the cable unit 4 is connected being fitted into the housing portion 3a of the housing 3, according to the second embodiment of the present invention.
Figure 20:
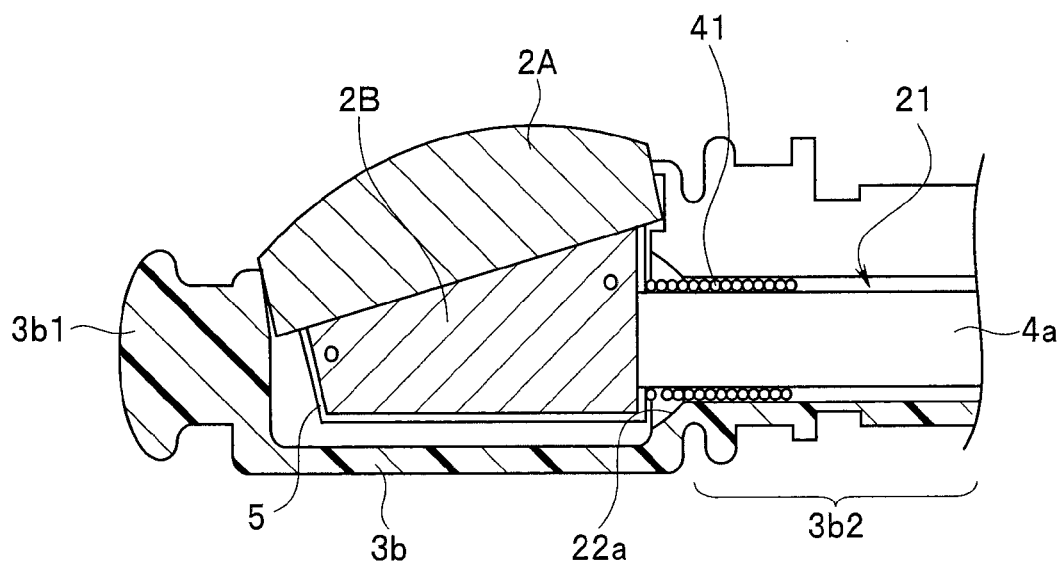
FIG. 20 is a sectional view showing a state in which the transducer unit 2 according to the second embodiment of the present invention is housed in the housing portion 3a of the housing 3.

FIG. 18, FIG. 19 and FIG. 20 are views for explaining the extension portion according to the present embodiment. FIG. 18 is a perspective view of the shield case 5 having the extension portion according to the present embodiment. FIG. 19 is a sectional view for explaining a process of the transducer unit 2 to which the cable unit 4 is connected being fitted into the housing portion 3a of the housing 3. FIG. 20 is a sectional view showing a state in which the transducer unit 2 of the present embodiment is housed in the housing portion 3a of the housing 3. In FIG. 18 to FIG. 20, the same components as in the first embodiment described above are assigned with the same reference signs, and the description thereof will be omitted.

In the present embodiment, the extension portion is configured by a coil spring member 41 that is a cylindrical spring. As shown in FIG. 18, the coil spring member 41 is a coil spring in which a metal wire is closely wound to each other. One end of the coil spring member 41 is fixedly attached to the lead-out port 17 which is formed on the side surface at the proximal end side of the shield case 5 by welding. The lead-out port 17 communicates with a hollow portion in an inside of the coil spring member 41. When the transducer unit 2 is housed in the shield case 5, the cable 4a passes in the hollow portion in the inside of the coil spring member 41.

Note that the coil spring member 41 described above is a single-winding coil spring, but the spring member which configures the extension portion may be a multiple-winding coil spring such as double-winding and triple-winding coil springs.

As shown in FIG. 19, the coil spring member 41 has elasticity, and therefore, when the shield case 5 is housed into the housing portion 3a, the coil spring member 41 enters the cable insertion path 21 while an outer circumferential side of the coil spring member 41 abuts on the upper side of the opening portion 22 of the cable insertion path 21 of the housing 3.

Therefore, in the process of housing the transducer unit 2 into the housing portion 3a of the housing 3, the connection portion of the cable unit 4 and the transducer unit 2 is protected by the extension portion 18, and bending stress to the connection portion of the cable unit 4 and the transducer unit 2 is relieved at the time of housing of the transducer unit 2 into the housing portion 3a of the housing 3.

Further, the present embodiment has the advantage that a length in an axial direction of the coil spring member 41 which is the extension portion is easily adjusted. Furthermore, if the length in the axial direction of the coil spring member 41 becomes longer, the shielding effectiveness for the cable 4a of the cable unit 4 can be enhanced more.

Consequently, according to the present embodiment described above, the ultrasound endoscope can be provided, which is capable of relieving stress concentration to the connection portion of the transducer unit and the cable unit, preventing buckling of the cable end, and preventing damage, breakage and the like of the signal line of the cable, at the time of assembly of the ultrasound endoscope. Further, according to the present embodiment described above, the assemblability of the distal end portion unit is enhanced, and yield is enhanced, which also leads to reduction in cost by extension.

Further, the coil spring member 41 as the extension portion also relieves bending stress to the lower side or the lateral direction, and therefore, relieves bending stress in every direction during working to be able to prevent damage, breakage and the like of the signal line of the cable.

For the purpose of positioning the transducer unit, a projected portion as in modification 2 of the first embodiment may be provided at the upper side of the coil spring member 41 of the present embodiment.

Furthermore, for the purpose of positioning around the axis of the transducer unit, the projected portion as in modification 4 of the first embodiment may be provided at the upper side of the coil spring member 41 of the present embodiment.

(Shortening of Transducer Unit)

Figure 21:
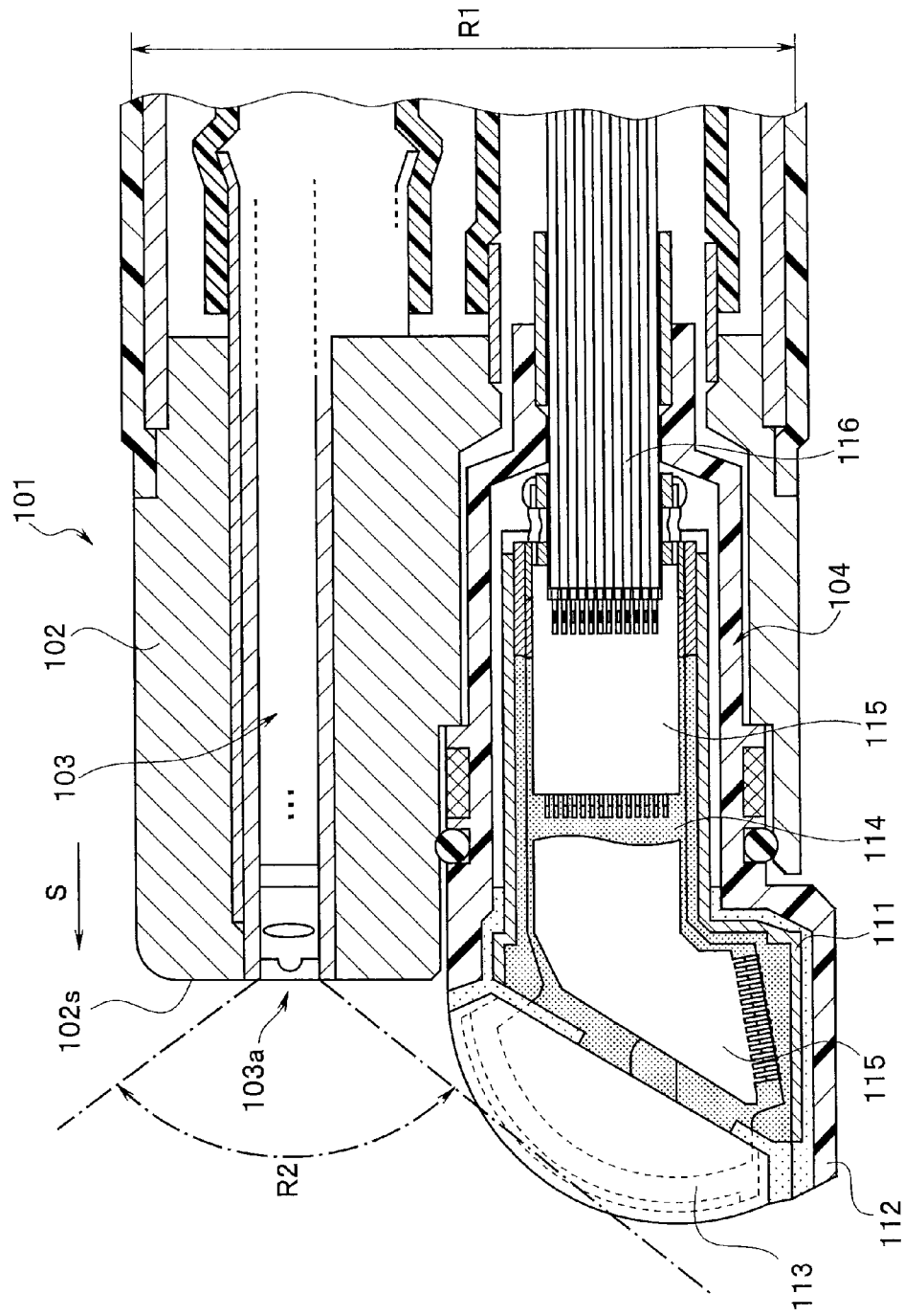
FIG. 21 is a partial cross-sectional view of the transducer unit fitted in a distal end rigid member with an image pickup unit.
Figure 22:
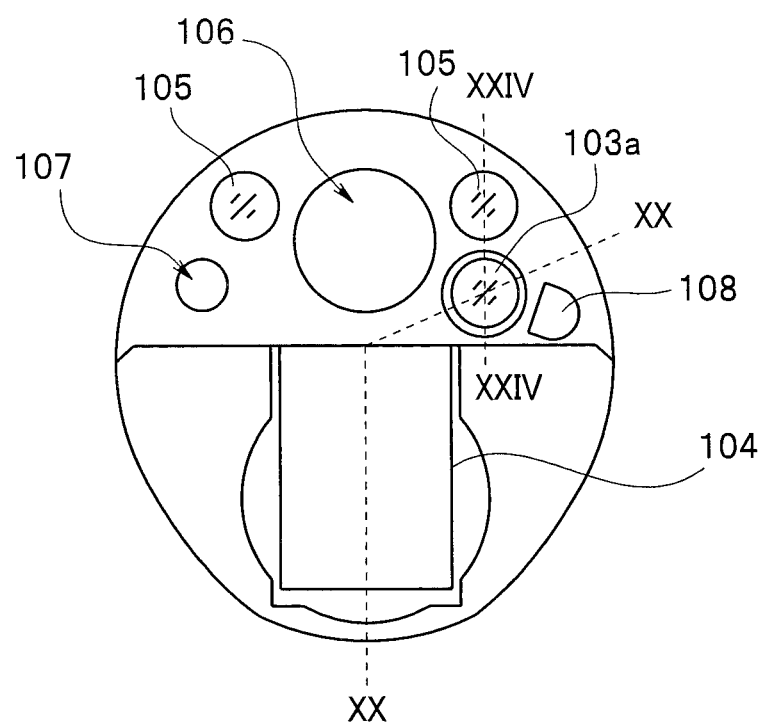
FIG. 22 is a view of an insertion portion of the ultrasound endoscope seen from a distal end side.

Incidentally, there is a case in which a distal end portion unit containing an ultrasound transducer is fitted in a distal end rigid member of an ultrasound endoscope with an image pickup unit including an image pickup device. FIG. 21 is a partial cross-sectional view of a transducer unit fitted in the distal end rigid member with the image pickup unit. FIG. 22 is a view of an insertion portion of the ultrasound endoscope seen from a distal end side. FIG. 21 is a sectional view taken along the XX-XX line of FIG. 22.

As shown in FIG. 21, a distal end portion 101 of the insertion portion of the ultrasound endoscope includes a distal end rigid member 102 having a size of R1 in a radial direction thereof.

In the distal end rigid member 102 an image pickup unit 103 containing an image pickup device and an objective optical system, and a transducer unit 104 are provided at a distal end side in an insertion direction S of the insertion portion.

Further, as shown in FIG. 21, the transducer unit 104 is provided to the distal end rigid member 102 so that a distal end in the insertion direction S of the transducer unit 104 protrudes forward in the insertion direction S from a distal end face 102s of the distal end rigid member 102.

Further, in the distal end rigid member 102, a treatment instrument insertion channel and an illumination unit (neither of them is illustrated) are provided, and in addition, an air/water feeding conduit not illustrated, a front water feeding conduit (see FIG. 22) and the like are also provided.

Further, as shown in FIG. 22, on the distal end face 102s, an objective optical system 103a which configures the image pickup unit 103, and an illumination optical system 105 which configures an illumination unit are provided, and an opening 106 of the treatment instrument inserting channel, an opening 107 of the front water feeding conduit, an air/water feeding nozzle 108 which is fixed to a distal end of the air/water feeding conduit which supplies a fluid to the objective optical system 103a and the like are provided.

The transducer unit 104 is configured by having a shield case 111, and a transducer case 112 in which the shield case 111 is inserted. In the shield case 111, an ultrasound transducer 113, a wiring board 114, a flexible board 115 and the like are provided. A distal end portion of a cable 116 is connected to the flexible board 115 in the shield case 111, and the cable 116 extends from a proximal end side of the transducer case 112.

In the case of FIG. 21, a distal end portion of the transducer unit 104 is within an image pickup range R2 of the image pickup unit 103, and therefore the distal end portion appears in an optical image. Namely, a part of an optical observation range is vignetted. An internal matter such as the wiring board 114 is present in the transducer unit 104, and therefore, when a length in the axial direction of the transducer unit 104 cannot be made short, vignetting as described above sometimes occurs.

Therefore, in this case, the length in an axial direction of the transducer unit 104 is shortened by an opening portion being provided at a part in the proximal end direction of the shield case 111 so that an internal matter (in this case, a proximal end portion 114a of the board 114) does not touch the shield case 111.

Figure 23:
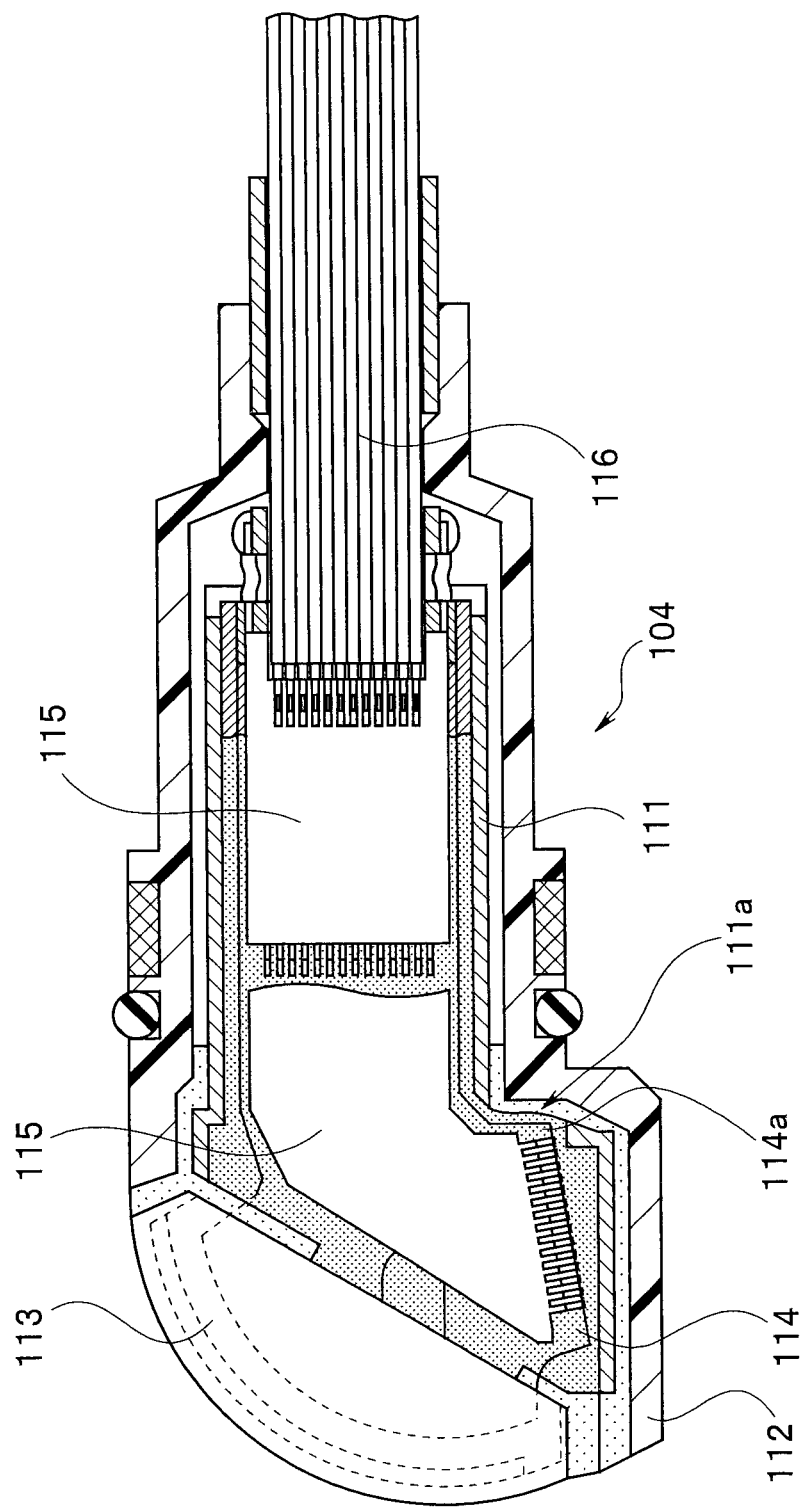
FIG. 23 is a partial cross-sectional view of the transducer unit provided with an opening portion in a part of a shield case 111.

FIG. 23 is a partial cross-sectional view of the transducer unit in which an opening portion is provided at a part of the shield case 111. As shown in FIG. 23, an opening portion 111a is provided at a part of the shield case 111 and at a proximal end side.

The opening portion 111a is provided at a position where the proximal end portion 114a of the wiring board 114 touches and interferes with the shield case 111 when the wiring board 114 is moved to the proximal end side.

Further, the opening portion 111a has such a shape that the wiring board 114 does not touch the shield case 111 when the wiring board 114 is moved to the proximal end side.

Consequently, the distal end portion of the transducer unit 104 can be further moved to the proximal end side, and therefore, appearance of the transducer unit 104 in the optical image can be prevented. Further, the length in the axial direction of the distal end rigid member can be also made short.
(Lens Fogging Prevention)

Figure 24:
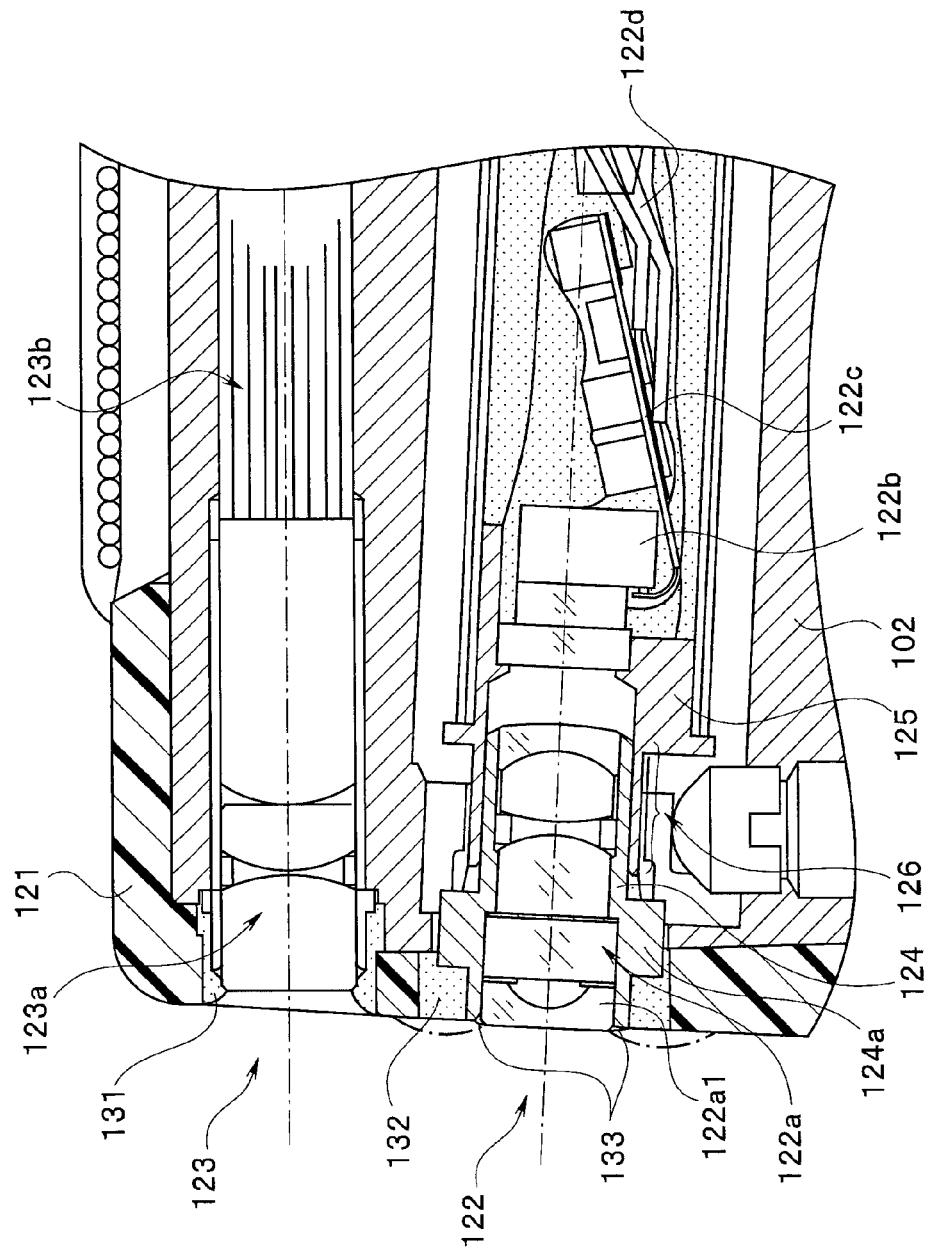
FIG. 24 is a partial cross-sectional view of a section of the image pickup unit and a light guide unit taken along an XXIV-XXIV line of FIG. 22.

Further, FIG. 24 is a partial cross-sectional view of the section of the image pickup unit and the light guide unit taken along the XXIV-XXIV line of FIG. 22. FIG. 24 is an example in which a resin cover 121 is fitted in a distal end side of the distal end rigid member 102. In FIG. 24, an image pickup unit 122 and a light guide unit 123 are shown.

The image pickup unit 122 includes an objective optical system 122a and an image pickup device 122b, and a cable 122d including a drive signal line and an image pickup signal line is connected via a circuit board 122c.

The image pickup unit 122 includes a lens frame 124 which holds the objective optical system 122a, and an image pickup device frame 125 including the image pickup device 122b. The lens frame 124 and the image pickup device frame 125 are both cylindrical frame members of stainless steel, and an outer circumferential portion of a proximal end side of the lens frame 124 is inserted and fitted in an inner circumferential portion of a distal end side of the image pickup device frame 125. An outer circumferential surface of the proximal end side of the lens frame 124 and an inner surface of the distal end side of the image pickup device frame 125 are coated with an adhesive, and after adjustment of an optical focal point position is performed, the adhesive is solidified, whereby the image pickup unit 122 is produced. In FIG. 24, a fitting region 126 of the outer circumferential portion of the proximal end side of the lens frame 124 and the inner circumferential portion of the distal end side of the image pickup device frame 125 is an adhesive surface.

The light guide unit 123 includes an illumination optical system 123a and an optical fiber bundle 123b. The light guide unit 123 is inserted from the distal end side of the distal end rigid member 102, and after the cover 121 is attached thereto, a periphery of the illumination window is coated with an adhesive 131, whereby the light guide unit 123 is fixed.

The image pickup unit 122 is fitted in the distal end rigid member 102 from the proximal end side of the distal end rigid member 102, and after the cover 121 is mounted, an adhesive 132 for a periphery of an observation window is coated, whereby the image pickup unit 122 is fixed.

The endoscope is heated to a high temperature for cleaning and disinfecting. When the endoscope is heated, the respective members, the adhesives and the like are thermally expanded, and because thermal expansion coefficients thereof differ from one another, the adhesives sometimes remove from the members.

Consequently, an outward flange portion 124a which projects in an outer circumferential direction is provided at a slightly central portion in an axial direction of the lens frame 124. The outward flange portion 124a is thick in a radial direction, and therefore, has high rigidity and an action to reduce deformation by thermal expansion. Namely, the lens frame 124 has the outward flange portion 124a, and therefore has high rigidity to such deformation that the lens frame 124 expands at the time of thermal expansion.

Further, a peripheral portion of the distal end side of the lens frame 124 is not covered with the cover 121, but is covered with the adhesive 132. Therefore, a periphery of the lens frame 124 is not covered with the cover 121, but is covered with the adhesive 132.

Furthermore, the adhesive is conventionally coated over the wide range around a distal end lens 122a1 of the objective optical system 122a as shown by the dashed line, whereas in this case, only a gap portion between the lens frame 124 and the distal end lens 122a1 is coated with an adhesive 133. For example, after the adhesive is temporarily coated as shown by the dashed line, the adhesive on the periphery of the distal end portion of the lens frame 124 is wiped away, whereby only the gap portion between the lens frame 124 and the distal end lens 122a1 can be coated with the adhesive 133.

Since the adhesive is conventionally coated onto the wide range shown by the dashed line, such stress as to expand the lens frame 124 occurs by thermal expansion by heating. Therefore, a gap occurs between the lens frame 124 and the distal end lens 122a1, moisture enters the interior from the gap, and so-called fogging sometimes occurs in the objective optical system 122a.

However, the outward flange portion 124a is provided at the lens frame 124, the periphery of the lens frame 124 is covered with the adhesive 132, the gap between the lens frame 124 and the distal end lens 122a1 is covered with the adhesive 133 as described above. Therefore, entry of moisture into the lens frame 124 due to thermal load by heating at the time of cleaning and disinfecting can be prevented.
(Mounting Cable)

Figure 25:
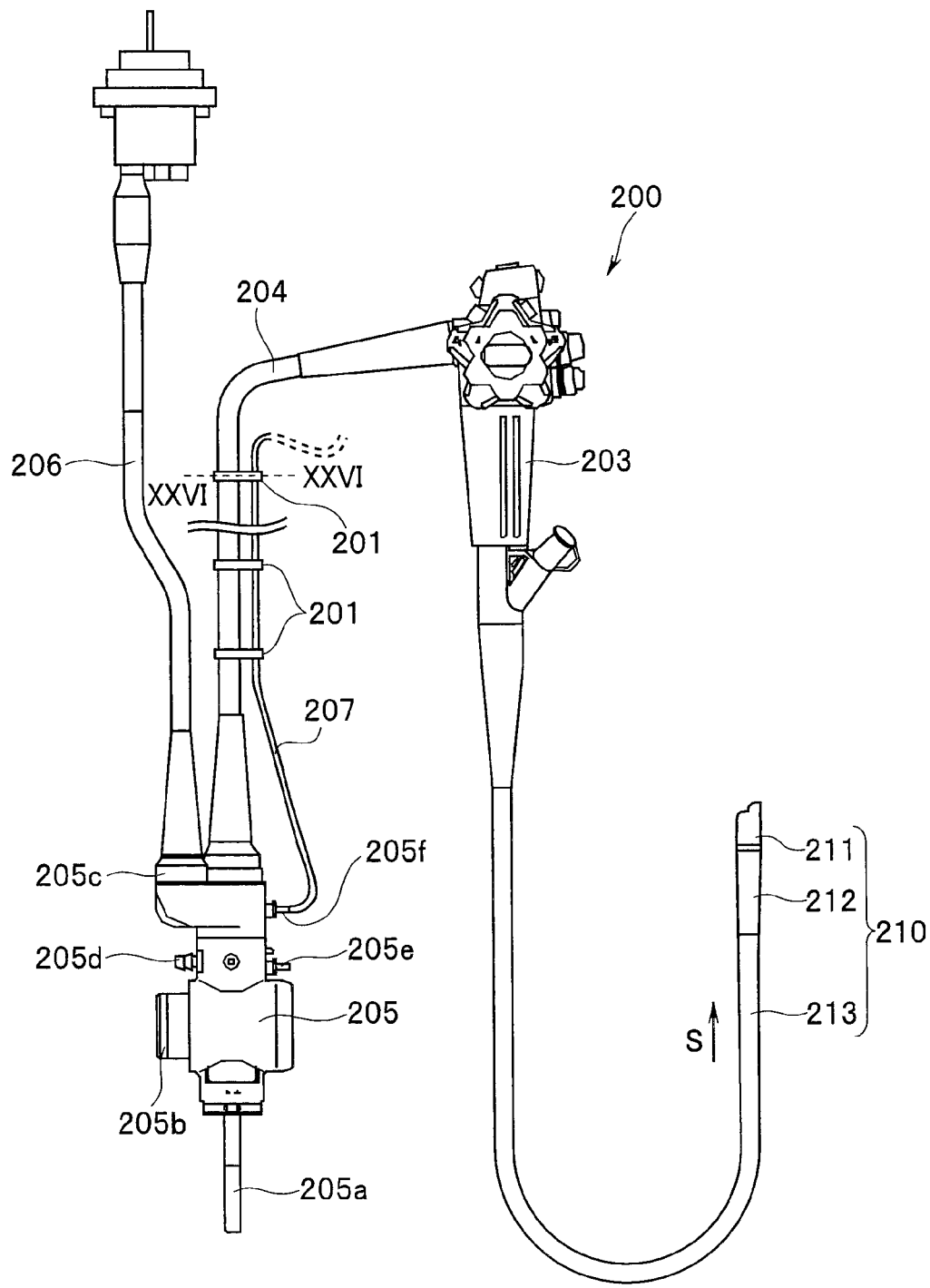
FIG. 25 is an external appearance view showing an external appearance of the ultrasound endoscope to which a tube is mounted.

Further, not only an ultrasound endoscope, but also an endoscope in general is sometimes used with a tube such as a water feeding tube being connected to the endoscope. FIG. 25 is an external appearance view showing an external appearance of an ultrasound endoscope to which a tube is mounted.

In an ultrasound endoscope 200 shown in FIG. 25, a main part is configured by an elongated insertion portion 210 which is inserted into a subject, an operation section 203 which is provided at a proximal end in the insertion direction S of the insertion portion 210, a universal cord 204 which is extended from the operation section 203 and has flexibility, and a connector 205 provided at an extension end of the universal cord 204.

The connector 205 is provided with a light source connector 205a, an electric connector 205b, an ultrasound connector 205c, a suction pipe sleeve 205d, an air/water feeding pipe sleeve 205e and an auxiliary water feeding pipe sleeve 205f.

A light source apparatus which supplies illuminating light is attachable and detachable to and from the light source connector 205a, and a video processor which performs various kinds of signal processing and the like via the signal cable is attachable and detachable to and from the electric connector 205b.

Further, an ultrasound observation apparatus is attachable and detachable to and from the ultrasound connector 205c via an ultrasound cable 206 which is connected to the ultrasound observation apparatus, and a suction pump is attachable and detachable to and from the suction pipe sleeve 205d via a suction tube. Further, a water feeding tank is attachable and detachable to and from the air/water feeding pipe sleeve 205e via an air/water feeding tube, and the water feeding tank is attachable and detachable to and from the auxiliary water feeding pipe sleeve 205f via a water feeding tube 207.

The insertion portion 210 is configured by a distal end portion 211, a bending portion 212 configured to be bendable in, for example, a vertical direction and a lateral direction, and a flexible tube portion 213 which is long and has flexibility being connectively provided in sequence from a distal end side in the insertion direction S.

Various tubes are mountable to the endoscope 200, but the auxiliary water feeding tube 207 will be described here, and the description of application to other tubes will be omitted.

One end of the auxiliary water feeding tube 207 is connected to the auxiliary water feeding pipe sleeve 205f, and the other end is connected to the water feeding tank (not illustrated). The auxiliary water feeding tube 207 is provided with mounting clips 201 at a plurality of spots at midpoints.

Figure 26:
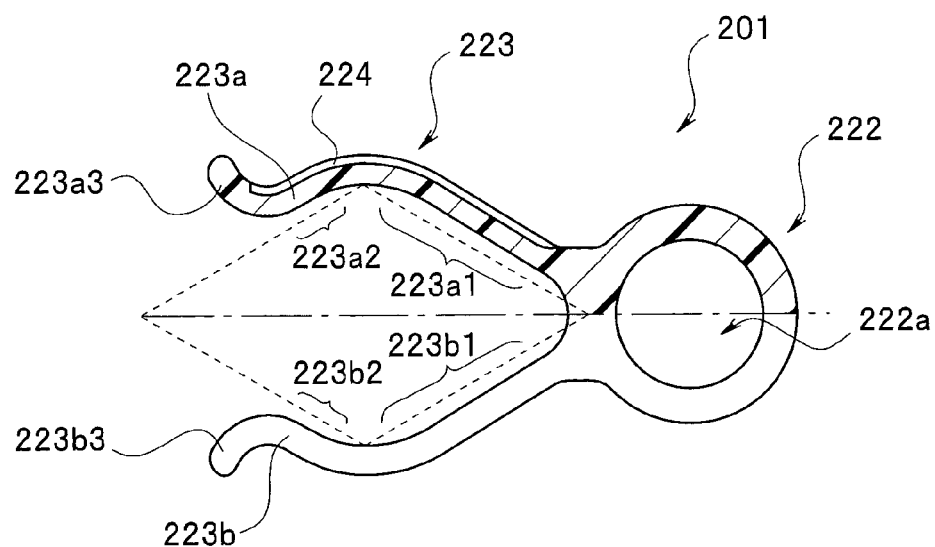
FIG. 26 is a partial cross-sectional view of a mounting clip 201, taken along an XXVI-XXVI line of FIG. 25.

FIG. 26 is a partial cross-sectional view of the mounting clip 201 taken along the XXVI-XXVI line of FIG. 25. The mounting clip 201 is made of a resin, and includes a ring portion 222 and an arm portion 223. In a hole portion 222a in a center of the ring portion 222, a tube such as the auxiliary water feeding tube 207 is inserted. Therefore, an opening diameter of the hole portion 222a has such a size that various tubes can be inserted therethrough.

The arm portion 223 includes two arms 223a and 223b, and the respective arms extend from the ring portion 222. The two arms 223a and 223b respectively include first portions 223a1 and 223b1 which extend from the ring portion 222, and second portions 223a2 and 223b2 which extend from distal end sides of the first portions, and connection portions of the first portions and the second portions are bent.

As shown in FIG. 26, the first portions 223a1 and 223b1 extend straightly, namely, substantially rectilinearly, the second portions 223a2 and 223b2 also have portions which are extended straightly, and an inner side portion sandwiched by the two arms 223a and 223b configures a grasping portion. The arm portion 223 is formed so that the grasping portion forms a substantially rhombic shape shown by the dotted line.

Accordingly, the two arms 223a and 223b are long as compared to the case in which the grasping portion is formed to be circular.

Grooves 224 are formed on outer sides of the two arms 223a and 223b.

Furthermore, open leg portions 223a3 and 223b3 are provided at distal end sides of the two arms 223a and 223b so that a cord or the like easily enters the grasping portion.

Figure 27:
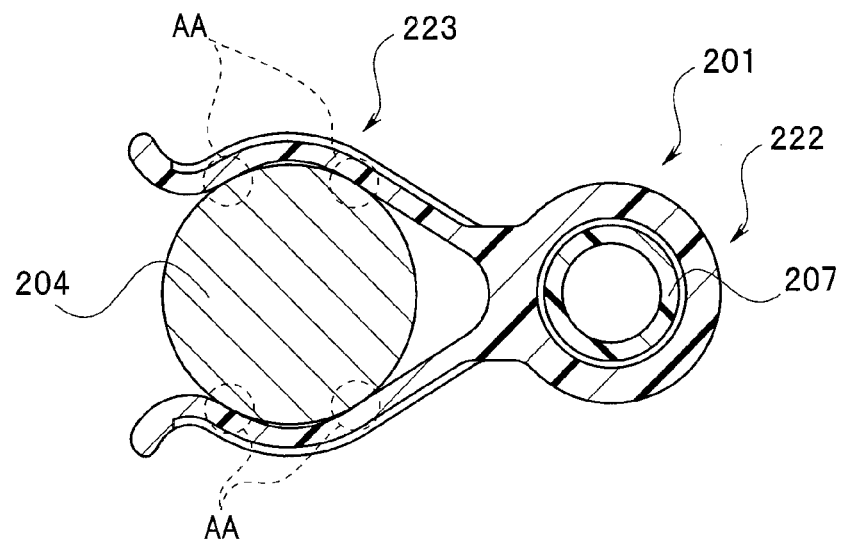
FIG. 27 is a sectional view showing a state in which the mounting clip 201 is mounted to a universal cord 204.

FIG. 27 is a sectional view showing a state in which the mounting clip 201 is mounted to the universal cord 204.

When the universal cord 204 is pressed against the grasping portion to be fitted therein in a state in which the auxiliary water feeding tube 207 is inserted through the hole portion 222a of the ring portion 222, the universal cord 204 is grasped by the arm portion 223 in such a manner as to be fitted in the grasping portion while a space between the distal end portions of the two arms 223a and 223b is opening.

At this time, the amount of the force which is required when the universal cord 204 is fitted to the arm portion 223 can be small because the grasping portion is rhombic and the arm portions 223, in particular, the first portions 223a1 and 223b1 are formed to be relatively long.

Furthermore, when the universal cord 204 is grasped by the grasping portion of the arm portion 223, contact of the universal cord 204 with a circular sectional shape and the two arms 223a and 223b is linear contact (or point contact) as shown in FIG. 27, and therefore, the amount of the force at the time of removal of the mounting clip 201 from the universal cord 204 can be small. In FIG. 27, the portions shown by the circles of the dotted lines represent the portions where the universal cord 204 and the respective arms linearly contact.

The connection portions of the first portions and the second portions of the arm portion 223 are bent so that the contact portions of the two arms 223a and 223b are linear contact to all kinds of the universal cords 204 to be fitted, whereby the removing force amount of the mounting clip from all the cords to which the mounting clip 201 is mounted can be made small.

According to the mounting clip 201 as above, mounting and dismounting of the mounting clip 201 to and from the universal cord 204 are enabled with a small force amount. Further, the mounting clip 201 can be mounted to various cords with different diameters.

Note that in the example described above, the example of mounting the mounting clip mounted to the auxiliary water feeding tube 207 to the universal cord 204 is described, but the mounting clip can be similarly applied to other tubes or other mount target cords.

In order not to bring the universal cord 204 and the mounting clip 201 into close contact with each other, a surface state of the inner side portion of the arm portion 223 of the mounting clip 201 may be intentionally made coarse, or may be made to have small irregularities. Thereby, a frictional force between the universal cord 204 and the mounting clip 201 can be reduced, and the universal cord 204 can be prevented from being damaged.

Figure 28:
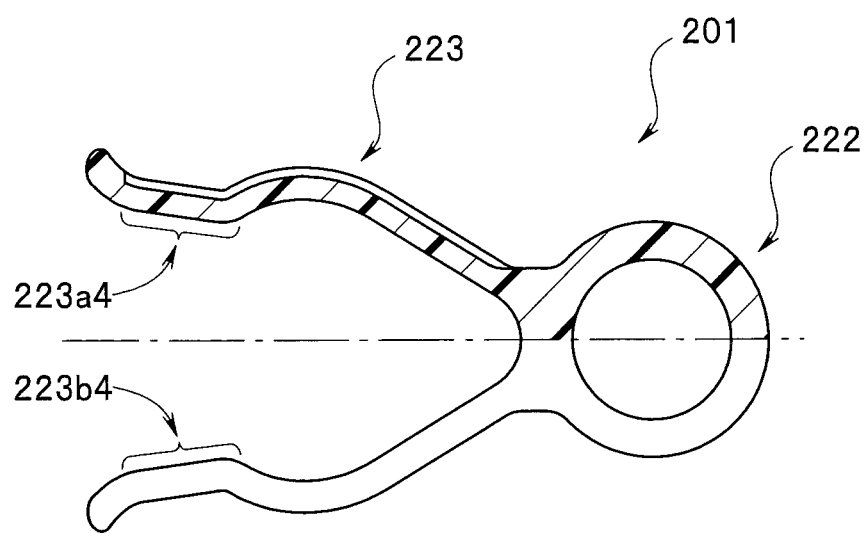
FIG. 28 is a view of the mounting clip 201 provided with extension portions at arm portion distal ends.

FIG. 28 is a view of the mounting clip 201 provided with extension portions at the arm portion distal ends. As shown in FIG. 28, the open leg portions 223a3 and 223b3 at the arm portion 223 distal end of the mounting clip 201 may be extended, and outwardly splaying extension portions 223a4 and 223b4 may be provided. By adoption of such a shape, when the mounting clip 201 is mounted to the universal cord 204, the arm portion 223 is gradually forced to be opened by the outwardly splaying extension portions 223a4 and 223b4, whereby the amount of the force required when the mounting clip 201 is fitted to the universal cord 204 can be made smaller.

According to the respective embodiments and the respective modifications thereof described above, stress concentration to the connection portion of the transducer unit and the cable unit, that is, stress concentration to the cable end is relieved, buckling of the cable end is prevented, and breakage of the signal line of the cable can be prevented, at the time of assembly of the ultrasound endoscope.

The present invention is not limited to the embodiments described above, and various modifications, alterations and the like can be made within the range without departing from the gist of the present invention.

What is claimed is:

1. An ultrasound endoscope, comprising:
    an ultrasound transmitting and receiving portion that has a top surface, a bottom surface and a side surface that connects the top surface and the bottom surface, and performs transmission and reception of ultrasound on the top surface side;
    a cable that is for transmitting and receiving an electrical signal to and from the ultrasound transmitting and receiving portion and is connected to the side surface of the ultrasound transmitting and receiving portion, the cable having a first surface that is adjacent to a connection portion for connection with the ultrasound transmitting and receiving portion and is oriented in the same direction as a direction of the top surface of the ultrasound transmitting and receiving portion;
    a conductive shield case that covers the side surface of the ultrasound transmitting and receiving portion and the bottom surface of the ultrasound transmitting and receiving portion, the shield case including, at a portion that covers the side surface, a lead-out port as a first opening formed for leading out the cable in a state of the ultrasound transmitting and receiving portion being housed in the shield case;
    an extension portion that is connected to an outer surface of the shield case adjacent to the lead-out port and extends in a leading-out direction of the cable by a predetermined distance so as to cover at least the first surface of the cable when the ultrasound transmitting and receiving portion is housed in the shield case, the extension portion having elasticity;
    a housing that holds the ultrasound transmitting and receiving portion via the shield case;
    a second opening that is provided in the housing for leading out the cable connected to the ultrasound transmitting and receiving portion when the ultrasound transmitting and receiving portion is fitted into the housing; and
    a cable insertion path that is provided in the housing and communicates with the second opening for inserting the cable therein.

2. The ultrasound endoscope according to claim 1, wherein the extension portion has a plate shape or a curved surface shape.

3. The ultrasound endoscope according to claim 1, wherein the extension portion is a spring formed by winding an elastic material in a helical shape into which the cable is inserted.

4. The ultrasound endoscope according to claim 1,
    wherein the cable insertion path is provided with a recessed portion formed by a part of an inner surface of the cable insertion path being recessed,
    the extension portion is provided with a projected portion which is a part of the extension portion being projected, and
    when the ultrasound transmitting and receiving portion is housed in the housing via the shield case, the recessed portion and the projected portion are fitted to each other.

5. The ultrasound endoscope according to claim 1,
    wherein the cable insertion path is provided with a projected portion which is a part of an inner surface of the cable insertion path being projected to the inner surface side,
    the extension portion is provided with a recessed portion formed by a part of the extension portion being recessed, and
    when the ultrasound transmitting and receiving portion is housed in the housing via the shield case, the projected portion and the recessed portion are fitted to each other.

6. The ultrasound endoscope according to claim 1,
    wherein the extension portion is provided with a protruded portion formed along an extending direction of the extension portion, and
    the housing is provided with a depressed portion in which the protruded portion is fitted.

7. The ultrasound endoscope according to claim 1, wherein the cable insertion path of the housing is provided with a step portion on which the extension portion abuts.

8. The ultrasound endoscope according to claim 1, wherein the cable insertion path of the housing is provided with a groove in which the extension portion enters.

9. The ultrasound endoscope according to claim 1, wherein a taper portion is formed at an opening portion of the cable insertion path of the housing.

* * * * *